United States Patent [19]

Arakawa et al.

[11] Patent Number: 5,750,552
[45] Date of Patent: *May 12, 1998

[54] IMIDAZOLINE DERIVATIVE, POSSIBLE TAUTOMER THEREOF, AND VULNERARY INCLUDING SUCH DERIVATIVE OR TAUTOMER

[75] Inventors: Eitaro Arakawa; Tetsuo Kato, both of Nagoya; Tsukasa Takamura, Toyota; Keiji Imai, Aichi-ken; Tetsuya Segami; Yukitaka Nakamura, both of Nagoya, all of Japan

[73] Assignee: Arax Co., Ltd., Japan

[*] Notice: The term of this patent shall not extend beyond the expiration date of Pat. No. 5,733,922.

[21] Appl. No.: 622,469

[22] Filed: Mar. 25, 1996

[30] Foreign Application Priority Data

Mar. 27, 1995 [JP] Japan ................... 7-067798

[51] Int. Cl.$^6$ ................... A61K 31/415; C07D 233/84
[52] U.S. Cl. ................... 514/386; 548/320.1
[58] Field of Search ................... 548/320.1; 514/386

[56] References Cited

U.S. PATENT DOCUMENTS

| | | |
|---|---|---|
| 4,255,431 | 3/1981 | Junggren et al. . |
| 4,337,257 | 6/1982 | Junggren et al. . |
| 4,508,905 | 4/1985 | Junggren et al. . |
| 5,106,863 | 4/1992 | Hajos et al. ................... 514/395 |

FOREIGN PATENT DOCUMENTS

| | | |
|---|---|---|
| 0 301 422 | 2/1989 | European Pat. Off. . |
| 0 354 788 | 2/1990 | European Pat. Off. . |
| 0 412 529 A1 | 2/1991 | European Pat. Off. . |

OTHER PUBLICATIONS

Chemical and Pharmaceutical Bulletin, vol. 40, No. 3, 1992, Japan, pp. 675–682, Tomio Yamakawa et al., "Synthesis and Structure–Activity Relationships of Substituted 2-[(2-Imidazolylsulfinylmethyl]anilines as a new class of gastric H+/K+–ATPase Inhibitors II".

Chemical and Pharmaceutical Bulletin, vol. 39, No. 7, 1991, Japan, pp. 1746–1752, Tomio Yamakawa et al.: "Synthesis and Structure–Activity Relatiosnhips of N–Substituted 2-[(2-Imidazolylsulfinyl)methl]anilines as a new class of gastric H+/K+ATPase inhibitors".

*Primary Examiner*—Patricia L. Morris
*Attorney, Agent, or Firm*—Parkhurst & Wendel, L.L.P.

[57] ABSTRACT

An imidazoline derivative or possible tautomer thereof, represented by the formula (1), wherein n represents one of integers "1" through "4", and $R_1$ and $R_2$ represent hydrogen atom, lower alkyl, aryl, aralkyl group, or $R_1$ and $R_2$ cooperate to represent alkylene, alkylidene or arylalkylidene group, while $R_3$ represents a nitrogen-containing aromatic ring that may be substituted by lower alkyl, alkoxy or alkanoyl group, or a substituted phenyl group represented by the formula (2), wherein $R_4$ and $R_5$ represent hydrogen atom, lower alkyl group that may be substituted by halogen atom or hydroxyl group, cycloalkylalkyl group, lower alkenyl group, lower alkanoyl group that may be substituted by halogen atom, lower alkoxyalkyl or alkoxycarbonyl group, arylcarbonyl, arylalkyl or arylalkoxycarbonyl group, lower alkylaminocarbonyl or alkylsulfonyl group or arylsulfonyl group, or $R_4$ and $R_5$ cooperate with an adjacent nitrogen atom to constitute a cyclic structure, while $R_6$ represents hydrogen atom, hydroxyl group, halogen atom, lower alkyl or alkoxy group or nitro group.

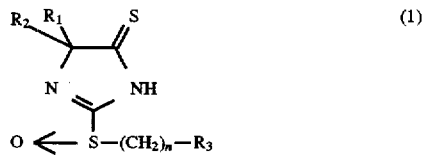

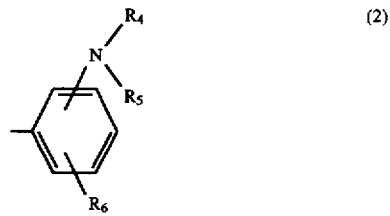

12 Claims, No Drawings

IMIDAZOLINE DERIVATIVE, POSSIBLE TAUTOMER THEREOF, AND VULNERARY INCLUDING SUCH DERIVATIVE OR TAUTOMER

BACKGROUND OF THE INVENTION

1. Field of the Invention

The present invention relates to novel imidazoline derivatives, possible tautomers thereof, a vulnerary or an anti-ulcer drug including such an imidazoline derivative or tautomer.

2. Discussion of the Prior Art

It is generally known that peptic ulcers such as gastric ulcer and duodenal ulcer are induced by imbalance between aggressive factors such as gastric acid and pepsin, and protective factors such as mucos, mucosal barrier and mucosal blood flow. Conventionally, therefore, various drugs for remedy of peptic ulcers have been used for inhibiting or suppressing the aggressive factors and/or promoting or intensifying the protective factors.

Typical examples of the aggressive factor inhibiting drugs that have been used are $H_2$-histamine receptor antagonists such as Cimetidine (available from Smith Kline & French Laboratories, United Kingdom) and Ranitidine (available from Glaxo, United Kingdom), and $H^+/K^+$ adenosine triphosphatase inhibitors (proton pump inhibitors) such as Omeprazole (available from Aktebolag Hassle, Sweden).

However, such drugs have various problems, and do not exhibit a sufficient effect. Described in detail, the $H_2$-histamine receptor antagonists provide an excellent effect to improve the symptoms of ulcer, but are likely to induce a recurrence of ulcer by a rebound of a dose thereof, undesirably requiring a continuous dosage thereof for a long period of time. The proton pump inhibitors, on the other hand, is characterized by a relatively long activity, but has some potential drawbacks due to its tendency to cause anacidity in the stomach, for instance, proliferation of bacteria and an increase of N-nitroso compounds produced in the stomach, leading to clinically undesirable hypergastrinemia.

As the protective factor promoting drugs, there are known cetraxate, sofalcone and teprenone. However, these drugs are not satisfactory in their effects per dose, and their effects to improve the subjective symptoms tend to be small. Therefore, their application is limited to concurrent use with the aggressive factor inhibiting drugs.

Thus, the anti-ulcer drugs currently available have the problems indicated above. The known aggressive factor inhibiting drugs and protective factor promoting drugs both suffer from unsatisfactory effects. In view of this prior art situation, there is a strong desire to develop an anti-ulcer drug which exhibits excellent effects of not only inhibiting the aggressive factors but also promoting the protective factors and which has a high degree of safety.

SUMMARY OF THE INVENTION

As a result of extensive research and study by the present inventors in an effort to solve the prior art problems, the inventors have found that some of compounds having an imidazoline structure exhibit excellent effects of promoting production of a basic Fibroblast Growth Factor (bFGF), inhibiting the aggressive factors and promoting the protective factors, and have a high degree of safety.

According to a first aspect of the present invention, there is provided an imidazoline derivative or a possible tautomer thereof, which is represented by the following formula (13)

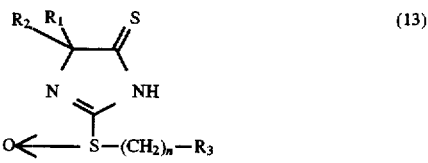

wherein n represents one of integers "1" through "4", and $R_1$ and $R_2$ represent a same one or respective different ones of a hydrogen atom, a lower alkyl group, an aryl group that may have a substituent group, and an aralkyl group, or cooperate to represent one of an alkylene group, an alkylidene group and an arylalkylidene group that may have a substituent group, while $R_3$ represents a nitrogen-containing aromatic ring that may be substituted by at least one of a lower alkyl group, a lower alkoxy group and a lower alkanoyl group, or a substituted phenyl group represented by the following formula (14),

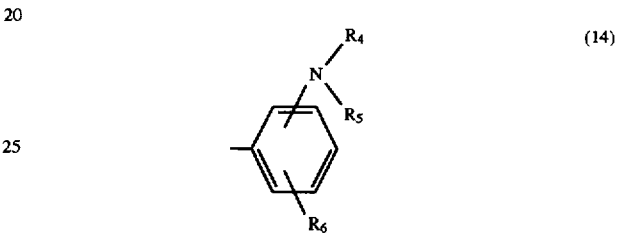

wherein $R_4$ and $R_5$ represent a same one or respective different ones of a hydrogen atom, a lower alkyl group that may be substituted by at least one halogen atom or at least one hydroxyl group, a cycloalkylalkyl group, a lower alkenyl group, a lower alkanoyl group that may be substituted by at least one halogen atom, a lower alkoxyalkyl group, a lower alkoxycarbonyl group, an arylcarbonyl group, an arylalkyl group, an arylalkoxycarbonyl group, a lower alkylaminocarbonyl group, a lower alkylsulfonyl group and an arylsulfonyl group, or $R_4$ and $R_5$ cooperate with an adjacent nitrogen atom to constitute a cyclic or ring structure, while $R_6$ represents one of a hydrogen atom, a hydroxyl group, a halogen atom, a lower alkyl group, a lower alkoxy group and a nitro group.

It is noted that the tautomer of the imidazoline derivative is represented by one of the following formulas (15-1) and (15-2).

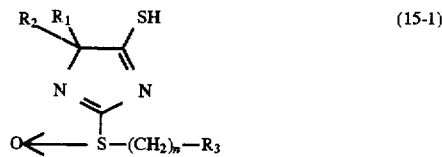

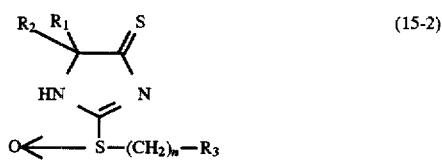

wherein $R_1$, $R_2$, $R_3$ and n are the same as specified above.

According to one preferred form of the first aspect of the invention, $R_1$ and $R_2$ in the above-identified formula (13), (15-1) and (15-2) represent a same one or respective different ones of a hydrogen atom, an alkyl group having 1–7 carbon atoms and a phenyl group that may have a substituent group, or cooperate to represent one of an alkylidene group having 2–5 carbon atoms, a benzylidene or cinnamylidene group that may have a substituent group, and an alkylene group having 2–6 carbon atoms, R₃ in the above-identified formulas (15-1) and (15-2) representing one of an alkyl group having 1–4 carbon atoms, an alkoxy group having 1–4 carbon atoms, a pyridyl or quinolyl group that may be substituted by a phenylalkyl group that may have a substituent group, and a substituted phenyl group represented by the above-identified formula (14), and wherein R₄ and R₅ in the-identified formula (14) represent a same one or respective ones of a hydrogen atom, an alkyl group having 1–7 carbon atoms that may be substituted by at least one halogen atom or at least one hydroxyl group, a cycloalkylalkyl group whose linear alkyl portion has 0–2 carbon atoms and whose cycloalkyl portion has 3–6 carbon atoms, an alkenyl group having 1–7 carbon atoms, an alkanoyl group having 1–7 carbon atoms that may be substituted by at least one halogen atom; an alkoxyalkyl group having 1–7 carbon atoms that may be substituted by at least one halogen atom, an alkoxycarbonyl group having 1–7 carbon atoms that may be substituted by at least one halogen atom, an arylcarbonyl group, an arylalkyl group, an arylalkoxycarbonyl group, an alkylaminocarbonyl group having 1–7 carbon atoms, an alkylsulfonyl group having 1–7 carbon atoms and an arylsulfonyl group, or $R_4$ and $R_5$ cooperate with an adjacent nitrogen atom to constitute a cyclic structure, while $R_6$ represents one of a hydrogen atom, a hydroxyl group, a halogen atom, an alkyl group having 1–5 carbon atoms, an alkoxy group having 1–5 carbon atoms and a nitro group.

According to a further preferred form of the first aspect of the invention, $R_3$ is a substituted phenyl group represented by the above-identified formula (14) and n is equal to 1.

The imidazoline derivative of the present invention as described above may be produced according to a second aspect of the present invention which provides a process of producing an imidazoline derivative or possible tautomer thereof, wherein the imidazoline derivative which is represented by the following formula (16) is produced by effecting a reaction of a 2, 4-dithiohydantoin compound or possible tautomer thereof represented by the following formula (17) with a compound represented by the following formula (18), so as to produce a compound or possible tautomer thereof which is represented by the following formula (19), and then oxidizing the compound or the tautomer.

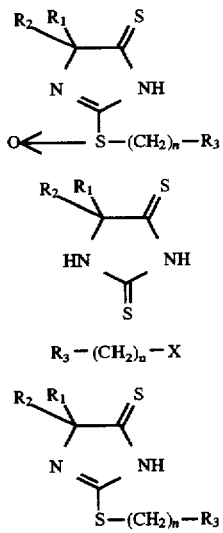

wherein n represents one of integers "1" through "4", X represents a halogen atom, and $R_1$ and $R_2$ represent a same one or respective different ones of a hydrogen atom, a lower alkyl group, an aryl group that may have a substituent group, and an aralkyl group, or cooperate to represent one of an alkylene group, an alkylidene group and an arylalkylidene group that may have a substituent group, and wherein R₃ represents a nitrogen-containing aromatic ring that may be substituted by at least one of a lower alkyl group, a lower alkoxy group and a lower alkanoyl group, or a substituted phenyl group represented by the following formula (20),

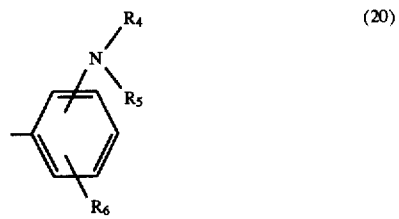

wherein $R_4$ and $R_5$ represent a same one or respective different ones of a hydrogen atom, a lower alkyl group that may be substituted by at least one halogen atom or at least one hydroxyl group, a cycloalkylalkyl group, a lower alkenyl group, a lower alkanoyl group that may be substituted by at least one halogen atom, a lower alkoxyalkyl group, a lower alkoxycarbonyl group, an arylcarbonyl group, an arylalkyl group, an arylalkoxycarbonyl group, a lower alkylaminocarbonyl group, a lower alkylsulfonyl group and an arylsulfonyl group, or $R_4$ and $R_5$ cooperate with an adjacent nitrogen atom to constitute a cyclic structure, while $R_6$ represents one of a hydrogen atom, a hydroxyl group, a halogen atom, a lower alkyl group, a lower alkoxy group and a nitro group.

In the above structural formulas and substituents (13) through (20), the term "lower" means that the corresponding group has about 1–10 carbon atoms. Further, the aliphatic hydrocarbon portions of the alkyl group, alkenyl group and alkoxy group may be either linear or branched.

According to a third aspect of the invention, there is provided a vulnerary including as an effective component a novel imidazoline derivative or possible tautomer thereof, which derivative is represented by the above formula (13), for example. It is noted that the term "vulnerary" is used in a broad sense. That is, the vulnerary includes a remedy for ulcer, for instance. The vulnerary according to the present invention is advantageously used as an anti-ulcer drug.

DETAILED DESCRIPTION OF THE INVENTION

In the above formula (13), $R_1$ and $R_2$ represent the same or respective different ones of a hydrogen atom, a linear or branched lower alkyl group, a phenyl group, a benzyl group and a p-hydroxybenzyl group. The lower alkyl group may be a methyl group, an ethyl group, a propyl group, a butyl group, a pentyl group, a hexyl group, a heptyl group, an isopropyl group, an isobutyl group, an isopentyl group, an isohexyl group or an isoheptyl group. Alternatively, $R_1$ and $R_2$ cooperate to represent one of a methylidene group, an ethylidene group, a propylidene group, an isopropylidene group, a benzylidene group, a cinnamylidene group, a trimethylene group, a tetramethylene group, a pentamethylene group and a hexamethylene group.

$R_3$ in the above formula (13) may represent one of a 2-dimethylaminophenyl group, a 3-dimethylaminophenyl group, a 4-dimethylaminophenyl group, a 2-dimethylamino-4-fluorophenyl group, a 2-dimethylamino-5-fluorophenyl group, 2-dimethylamino-3-chlorophenyl group, a 2-dimethylamino-4-chlorophenyl group, a 2-dimethylamino-5-chlorophenyl group, a 2-dimethylamino-6-chlorophenyl group, a 2-dimethylamino-5-bromophenyl group, a 2-dimethylamino-3-methylphenyl group, a 2-dimethylamino-4-methylphenyl group, a 2-dimethylamino-5-methylphenyl group, a 2-dimethylamino-6-methylphenyl group, a 2-dimethylamino-4-nitrophenyl group, a 2-dimethylamino-5-nitrophenyl group, a 5-hydroxy-2-dimethylaminophenyl group, a 2-dimethylamino-3-methoxyphenyl group, a 2-dimethylamino-5-methoxyphenyl group, a 2-dimethylamino-4,5-dimethoxyphenyl group, a 2-N-ethyl-N-methylaminophenyl group, a 3-N-ethyl-N-methylaminophenyl group, a 4-N-ethyl-N-methylaminophenyl group, a 2-diethylaminophenyl group, a 3-diethylaminophenyl group, a 4-diethylaminophenyl group, a 2-N-propyl-N-methylaminophenyl group, a 3-N-propyl-N-methylaminophenyl group, a 4-N-propyl-N-methylaminophenyl group, a 2-N-isopropyl-N-methylaminophenyl group, a 3-N-isopropyl-N-methylaminophenyl group, a 4-N-isopropyl-N-methylaminophenyl group, a 2-N-butyl-N-methylaminophenyl group, a 3-N-butyl-N-methylaminophenyl group, a 4-N-butyl-N-methylaminophenyl group, a 2-N-isobutyl-N-methylaminophenyl group, a 3-N-isobutyl-N-methylaminophenyl group, a 4-N-isobutyl-N-methylaminophenyl group, a 2-N-tert-butyl-N-methylaminophenyl group, a 2-N-pentyl-N-methylaminophenyl group, a 2-N-isopentyl-N-methylaminophenyl group, a 2-N-hexyl-N-methylaminophenyl group, a 2-N-isohexyl-N-methylaminophenyl group, a 2-N-heptyl-N-methylaminophenyl group, a 2-N-isoheptyl-N-methylaminophenyl group, a 2-N-allyl-N-methylaminophenyl group, a 2-N-methoxymethyl-N-methylaminophenyl group, a 2-N-(2, 2, 2-trifluoroethyl)-N-methylaminophenyl group, a 2-N-cyclopropylmethyl-N-methylaminophenyl group, a 2-N-(2-cyclopropylethyl)-N-methylaminophenyl group, a 2-N-methoxycarbonyl-N-methylaminophenyl group, a 2-N-tert-butoxycarbonyl-N-methylaminophenyl group, a 2-N-benzyloxycarbonyl-N-methylaminophenyl group, a 2-N-(2-chloroethyl)-N-methylaminophenyl group, a 2-N-(2-hydroxyethyl)-N-methylaminophenyl group, a 2-N-methylaminocarbonyl-N-methylaminophenyl group, a 2-N-ethylaminocarbonyl-N-methylaminophenyl group, a 2-N-propylaminocarbonyl-N-methylaminophenyl group, a 2-N-butylaminocarbonyl-N-methylaminophenyl group, a 2-N-isopropylaminocarbonyl-N-methylaminophenyl group, a 2-N-isobutylaminocarbonyl-N-methylaminophenyl group, a 2-N-methylsulfonyl-N-methylaminophenyl group, a 2-N-ethylsulfonyl-N-methylaminophenyl group, a 2-N-propylsulfonyl-N-methylaminophenyl group, a 2-N-butylsulfonyl-N-methylaminophenyl group, a 2-N-isopropylsulfonyl-N-methylaminophenyl group, a 2-N-isobutylsulfonyl-N-methylaminophenyl group, a 2-methylaminophenyl group, a 3-methylaminophenyl group, a 4-methylaminophenyl group, a 2-N-ethylaminophenyl group, a 2-N- (2, 2, 2-trifluoroethyl) aminophenyl group, 2-N-propylaminophenyl group, a 2-N-isopropylaminophenyl group, a 2-N-butylaminophenyl group, a 2-N-isobutylaminophenyl group, a 2-N-tert-butylaminophenyl group, a 2-N-pentylaminophenyl group, a 2-N-isopentylaminophenyl group, a 2-N-hexylaminophenyl group, a 2-N-isohexylaminophenyl group, a 2-N-heptylaminophenyl group, a 2-N-isoheptylaminophenyl group, a 2-N-cyclopropylmethylaminophenyl group, a 2-N-(2-cyclopropylethyl)aminophenyl group, a 2-N-allylaminophenyl group, a 2-N-methoxymethylaminophenyl group, a 2-N-methoxycarbonylaminophenyl group, a 2-N-ethoxycarbonylaminophenyl group, a 2-N-tert-butoxycarbonylaminophenyl group, a 2-N-benzyloxycarbonylaminophenyl group, a 2-aminophenyl group, a 3-aminophenyl group, a 4-aminophenyl group, a 2-N-acetylaminophenyl group, a 3-N-acetylaminophenyl group, a 4-N-acetylaminophenyl group, a 2-N-formyl-N-methylaminophenyl group, a 2-N-formylaminophenyl group, a 2-N-trifluoroacetylaminophenyl group, a 3-N-trifluoroacetylaminophenyl group, a 4-N-trifluoroacetylaminophenyl group, a 2-N-(2-chloroethyl) aminophenyl group, a 2-N-(2-hydroxyethyl) aminophenyl group, a 2-N-methylaminocarbonylaminophenyl group, a 2-N-ethylaminocarbonylaminophenyl group, a 2-N-propylaminocarbonylaminophenyl group, a 2-N-butylaminocarbonylaminophenyl group, a 2-N-isopropylaminocarbonylaminophenyl group, a 2-N-isobutylaminocarbonylaminophenyl group, a 2-N-methylsulfonylaminophenyl group, a 2-N-ethylsulfonylaminophenyl group, a 2-N-propylsulfonylaminophenyl group, a 2-N-butylsulfonylaminophenyl group, a 2-N-isopropylsulfonylaminophenyl group, a 2-N-isobutylsulfonylaminophenyl group, a 2-N-benzenesulfonylaminophenyl group, a 2-N-p-toluenesulfonylaminophenyl group, a 2-pyridyl group, a 3-pyridyl group, a 4-pyridyl group, a 4-methoxy-2-pyridyl group, 3,5-dimethyl-2-pyridyl group, a 3,4,5-trimethyl-2-pyridyl group, a 4-methoxy-5-methyl-2-pyridyl group, a 4-methoxy-3,5-dimethyl-2-pyridyl group, a 2-quinolinyl group, a 8-quinolinyl group, a 2-aziridinophenyl group, a 2-N-pyrrolidinophenyl group, a 2-piperidinophenyl group, a 2-morpholinophenyl group, a 2-maleimidephenyl group, a 2-phtalimidophenyl group.

Examples of the imidazoline derivative represented by the above formula (9) include the following:

(1) 2-(2-dimethylaminobenzylsulfinyl)-5,5-dimethylimidazolin-4-thione (2) 2-(2-dimethylaminobenzylsulfinyl)-5-ethyl-5-methylimidazolin-4-thione (3) 2-(2-dimethylaminobenzylsulfinyl)-5,5-diehylimidazolin-4-thione (4) 2-(2-dimethylaminobenzylsulfinyl)-5-phenyl-5-methylimidazolin-4-thione (5) 2-(2-N-ethyl-N-methylaminobenzylsulfinyl)-5,5-dimethylimidazolin-4-thione (6) 2-(2-N-propyl-N-methylaminobenzylsulfinyl)-5,5-dimethylimidazolin-4-thione (7) 2-(2-N-butyl-N-methylaminobenzylsulfinyl)-5,5-dimethylimidazolin-4-thione (8) 2-(2-N-pentyl-N-methylaminobenzylsulfinyl)-5,5-dimethylimidazolin-4-thione (9) 2-(2-N-hexyl-N-methylaminobenzylsulfinyl)-5,5-dimethylimidazolin-4-thione

(10) 2-(2-N-heptyl-N-methylaminobenzylsulfinyl)-5,5-dimethylimidazolin-4-thione

(11) 2-(2-N-isopropyl-N-methylaminobenzylsulfinyl)-5,5-dimethylimidazolin-4-thione

(12) 2-(2-N-isobutyl-N-methylaminobenzylsulfinyl)-5,5-dimethylimidazolin-4-thione

(13) 2-(2-N-isopentyl-N-methylaminobenzylsulfinyl)-5,5-dimethylimidazolin- 4-thione

(14) 2-(2-N-isohexyl-N-methylaminobenzylsulfinyl)-5,5-dimethylimidazolin-4-thione
(15) 2-(2-N-isoheptyl-N-methylaminobenzylsulfinyl)-5,5-dimethylimidazolin-4-thione
(16) 2-(2-N-tert-butyl-N-methylaminobenzylsulfinyl)-5,5-dimethylimidazolin-4-thione
(17) 2-(2-N-allyl-N-methylaminobenzylsulfinyl)-5,5-dimethylimidazolin-4-thione
(18) 2-[2-N-(2,2,2-trifluoroethyl)-N-methylaminobenzylsulfinyl]-5,5-dimethylimidazolin-4-thione
(19) 2-(2-dimethylamino-3-methylbenzylsulfinyl)-5,5-dimethylimidazolin-4-thione
(20) 2-(2-dimethylamino-5-methylbenzylsulfinyl)-5,5-dimethylimidazolin-4-thione
(21) 2-(2-dimethylamino-5-hydroxybenzylsulfinyl)-5,5-dimethylimidazolin-4-thione
(22) 2-(5-chloro-2-dimethylaminobenzylsulfinyl)-5,5-dimethylimidazolin-4-thione
(23) 2-(4-chloro-2-dimethylaminobenzylsulfinyl)-5,5-dimethylimidazolin-4-thione
(24) 2-(2-dimethylamino-5-methoxybenzylsulfinyl)-5,5-dimethylimidazolin-4-thione
(25) 2-(2-dimethylamino-4-fluorobenzylsulfinyl)-5,5-dimethylimidazolin-4-thione
(26) 2-(2-dimethylamino-4-nitrobenzylsulfinyl)-5,5-dimethylimidazolin-4-thione
(27) 2-(2-dimethylamino-5-nitrobenzylsulfinyl)-5,5-dimethylimidazolin-4-thione
(28) 2-(2-N-cyclopropylmethyl-N-methylaminobenzylsulfinyl)-5,5-dimethylimidazolin-4-thione
(29) 2-[2-N-(2-cyclopropylethyl)-N-methylaminobenzylsulfinyl]-5,5-dimethylimidazolin-4-thione
(30) 2-(2-N-methoxymethyl-N-methylaminobenzylsulfinyl)-5,5-dimethylimidazolin-4-thione
(31) 2-(2-N-methoxycarbonyl-N-methylaminobenzylsulfinyl)-5,5-dimethylimidazolin-4-thione
(32) 2-(2-N-ethoxycarbonyl-N-methylaminobenzylsulfinyl)-5,5-dimethylimidazolin-4-thione
(33) 2-(2-N-formyl-N-methylaminobenzylsulfinyl)-5,5-dimethylimidazolin-4-thione
(34) 2-(2-N-trifluoroacetyl-N-methylaminobenzylsulfinyl)-5,5-dimethylimidazolin-4-thione
(35) 2-(2-N-propyl-N-methylaminobenzylsulfinyl)-5-phenyl-5-methylimidazolin-4-thione
(36) 2-(2-N-butyl-N-methylaminobenzylsulfinyl)-5-phenyl-5-methylimidazolin-4-thione
(37) 2-(2-N-pentyl-N-methylaminobenzylsulfinyl)-5-phenyl-5-methylimidazolin-4-thione
(38) 2-(2-N-hexyl-N-methylaminobenzylsulfinyl)-5-phenyl-5-methylimidazolin-4-thione
(39) 2-(2-N-heptyl-N-methylaminobenzylsulfinyl)-5-phenyl-5-methylimidazolin- 4-thione
(40) 2-(2-N-isopropyl-N-methylaminobenzylsulfinyl)-5-phenyl-5-methylimidazolin-4-thione
(41) 2-(2-N-isobutyl-N-methylaminobenzylsulfinyl)-5-phenyl-5-methylimidazolin-4-thione
(42) 2-(2-N-isopentyl-N-methylaminobenzylsulfinyl)-5-phenyl-5-methylimidazolin-4-thione
(43) 2-(2-N-isohexyl-N-methylaminobenzylsulfinyl)-5-phenyl-5-methylimidazolin-4-thione
(44) 2-(2-N-isoheptyl-N-methylaminobenzylsulfinyl)-5-phenyl-5-methylimidazolin-4-thione
(45) 2-(2-N-tert-butyl-N-methylaminobenzylsulfinyl)-5-phenyl-5-methylimidazolin-4-thione
(46) 2-(2-N-ethyl-N-methylaminobenzylsulfinyl)-5-phenyl-5-methylimidazolin-4-thione
(47) 2-(2-N-allyl-N-methylaminobenzylsulfinyl)-5-phenyl-5-methylimidazolin-4-thione
(48) 2-[2-N-(2,2,2-trifluoroethyl)-N-methylaminobenzylsulfinyl]-5-phenyl-5-methylimidazolin-4-thione
(49) 2-(2-N-formyl-N-methylaminobenzylsulfinyl)-5-phenyl-5-methylimidazolin-4-thione
(50) 2-(2-N-cyclopropylmethyl-N-methylaminobenzylsulfinyl)-5-phenyl-5-methylimidazolin-4-thione
(51) 2-[2-N-(2-cyclopropylethyl)-N-methylaminobenzylsulfinyl]-5-phenyl-5-methylimidazolin-4-thione
(52) 2-(2-N-methoxymethyl-N-methylaminobenzylsulfinyl)-5-phenyl-5-methylimidazolin-4-thione
(53) 2-(2-pyridylmethylsulfinyl)-5,5-dimethylimidazolin-4-thione
(54) 2-(4-methoxy-3,5-dimethyl-2-pyridylmethylsulfinyl)-5,5-dimethylimidazolin-4-thione
(55) 2-(8-quinolinylmethylsulfinyl)-5,5-dimethylimidazolin-4-thione
(56) 2-(3-dimethylaminobenzylsulfinyl)-5,5-dimethylimidazolin-4-thione
(57) 2-(2-N-methylaminobenzylsulfinyl)-5,5-dimethylimidazolin-4-thione
(58) 2-(2-N-methoxycarbonylaminobenzylsulfinyl)-5,5-dimethylimidazolin-4-thione
(59) 2-(2-N-ethoxycarbonylaminobenzylsulfinyl)-5,5-dimethylimidazolin-4-thione
(60) 2-[2-N-( 2,2,2-trifluoroethyl)aminobenzylsulfinyl]-5,5-dimethylimidazolin-4-thione
(61) 2-(2-N-benzoylaminobenzylsulfinyl)-5,5-dimethylimidazolin-4-thione
(62) 2-(2-N-trifluoroacetylaminobenzylsulfinyl)-5,5-dimethylimidazolin-4-thione
(63) 2-(2-N-tert-butoxycarbonylaminobenzylsulfinyl)-5,5-dimethylimidazolin-4-thione
(64) 2-(2-N-benzyloxycarbonylaminobenzylsulfinyl)-5,5-dimethylimidazolin-4-thione
(65) 2-(2-N-formylaminobenzylsulfinyl)-5,5-dimethylimidazolin- 4-thione
(66) 2-(2-N-acetylaminobenzylsulfinyl)-5,5-dimethylimidazolin-4-thione
(67) 2-(2-aminobenzylsulfinyl)-5,5-dimethylimidazolin-4-thione
(68) 2-(2-aziridinobenzylsulfinyl)-5,5-dimethylimidazolin-4-thione
(69) 2-(2-pyrrolidinobenzylsulfinyl)-5,5-dimethylimidazolin-4-thione
(70) 2-(2-piperazinobenzylsulfinyl)-5,5-dimethylimidazolin-4-thione
(71) 2-(2-maleimidebenzylsulfinyl)-5,5-dimethylimidazolin-4-thione
(72) 2-(2-phtalimidobenzylsulfinyl)-5,5-dimethylimidazolin-4-thione
(73) 2-[2-N-(2-chloroethyl)-N-methylaminobenzylsulfinyl]-5,5-dimethylimidazolin-4-thione
(74) 2-[2-N-(2-hydroxyethyl)-N-methylaminobenzylsulfinyl]-5,5-dimethylimidazolin-4-thione
(75) 2-(2-N-methylaminocarbonyl-N-methylaminobenzylsulfinyl)-5, 5-dimethylimidazolin-4-thione
(76) 2-(2-N-ethylaminocarbonyl-N-methylaminobenzylsulfinyl)-5, 5-dimethylimidazolin-4-thione

(77) 2-(2-N-propylaminocarbonyl-N-methylaminobenzylsulfinyl)-5,5-dimethylimidazolin-4-thione
(78) 2-(2-N-butylaminocarbonyl-N-methylaminobenzylsulfinyl)-5,5-dimethylimidazolin-4-thione
(79) 2-(2-N-isopropylaminocarbonyl-N-methylaminobenzylsulfinyl)-5,5-dimethylimidazolin-4-thione
(80) 2-(2-N-isobutylaminocarbonyl-N-methylaminobenzylsulfinyl)-5,5-dimethylimidazolin-4-thione
(81) 2-(2-N-methylaminocarbonylaminobenzylsulfinyl)-5,5-dimethylimidazolin-4-thione
(82) 2-[2-N-(2-chloroethyl)aminobenzylsulfinyl]-5,5-dimethylimidazolin-4-thione
(83) 2-[2-N-(2-hydroxyethyl)aminobenzylsulfinyl]-5,5-dimethylimidazolin-4-thione
(84) 2-(2-N-ethylaminocarbonylaminobenzylsulfinyl)-5,5-dimethylimidazolin-4-thione
(85) 2-(2-N-propylaminocarbonylaminobenzylsulfinyl)-5,5-dimethylimidazolin-4-thione
(86) 2-(2-N-butylaminocarbonylaminobenzylsulfinyl)-5,5-dimethylimidazolin-4-thione
(87) 2-(2-N-isopropylaminocarbonylaminobenzylsulfinyl)-5,5-dimethylimidazolin-4-thione
(88) 2-(2-N-isobutylaminocarbonylaminobenzylsulfinyl)-5,5-dimethylimidazolin-4-thione
(89) 2-(2-N-methylsulfonyl-N-methylaminobenzylsulfinyl)-5,5-dimethylimidazolin-4-thione
(90) 2-(2-N-ethylsulfonyl-N-methylaminobenzylsulfinyl)-5,5-dimethylimidazolin-4-thione
(91) 2-(2-N-propylsulfonyl-N-methylaminobenzylsulfinyl)-5,5-dimethylimidazolin-4-thione
(92) 2-(2-N-butylsulfonyl-N-methylaminobenzylsulfinyl)-5,5-dimethylimidazolin-4-thione
(93) 2-(2-N-isopropylsulfonyl-N-methylaminobenzylsulfinyl)-5,5-dimethylimidazolin-4-thione
(94) 2-(2-N-isobutylsulfonyl-N-methylaminobenzylsulfinyl)-5,5-dimethylimidazolin-4-thione
(95) 2-(2-N-methylsulfonylaminobenzylsulfinyl)-5,5-dimethylimidazolin-4-thione
(96) 2-(2-N-ethylsulfonylaminobenzylsulfinyl)-5,5-dimethylimidazolin-4-thione
(97) 2-(2-N-propylsulfonylaminobenzylsulfinyl)-5,5-dimethylimidazolin-4-thione
(98) 2-(2-N-butylsulfonylaminobenzylsulfinyl)-5,5-dimethylimidazolin-4-thione
(99) 2-(2-N-isopropylsulfonylaminobenzylsulfinyl)-5,5-dimethylimidazolin-4-thione
(100) 2-(2-N-isobutylsulfonylaminobenzylsulfinyl)-5,5-dimethylimidazolin-4-thione
(101) 2-(2-N-benzenesulfonylaminobenzylsulfinyl)-5,5-dimethylimidazolin-4-thione
(102) 2-(2-N-p-toluenesulfonylaminobenzylsulfinyl)-5,5-dimethylimidazolin-4-thione
(103) 2-(2-diethylaminobenzylsulfinyl)-5,5-dimethylimidazolin-4-thione
(104) 2-(2-diethylaminobenzylsulfinyl)-5-phenyl-5-methylimidazolin-4-thione
(105) 2-(2-N-sec-butyl-N-methylaminobenzylsulfinyl)-5,5-dimethylimidazolin-4-thione
(106) 2-(2-N-sec-butyl-N-methylaminobenzylsulfinyl)-5-phenyl-5-methylimidazolin-4-thione
(107) 2-(2-N-cyclohexylmethyl-N-methylaminobenzylsulfinyl)-5,5-dimethylimidazolin-4-thione
(108) 2-(2-N-ethoxyoxalylaminobenzylsulfinyl)-5,5-dimethylimidazolin-4-thione
(109) 2-[8-(1-methyl-1,2,3,4-tetrahydroquinolinyl)methylsulfinyl]-5,5-dimethylimidazolin-4-thione A compound which is represented by the above formula (13) is prepared according to reactions (a) and (b) as indicated in the following formula (21) wherein $R_1$, $R_2$, $R_3$ and n are the same as in the above formulas (13) and (14), and X represents a halogen atom.

Described in detail, compounds (III), (IV) and (V) are obtained by the reaction (a) between compounds (I) and (II). Among the thus obtained compounds (III), (IV) and (V), the compound (III) is isolated. A desired compound (VI) is obtained by the reaction (b) by oxidizing the thus obtained compound (III) in a suitable solvent, using an oxidizing agent.

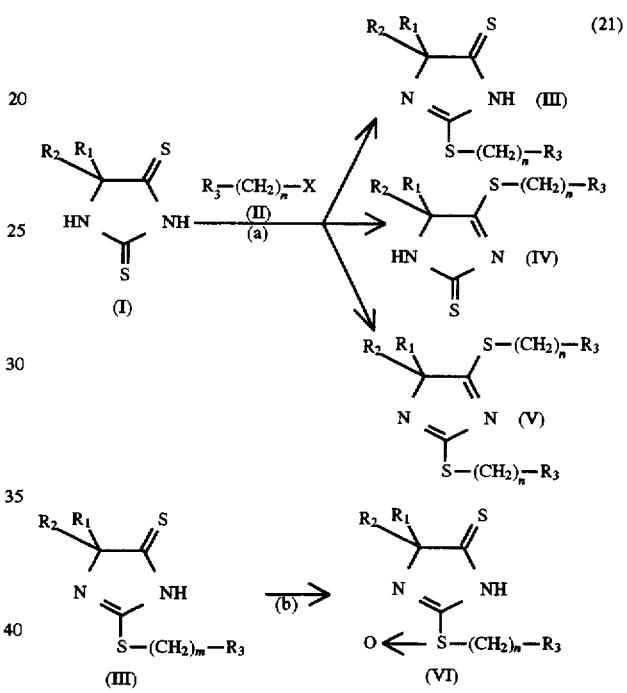

Explained more specifically, the compound (I) as a starting material used for the reaction (a) is generally commercially available, or may be prepared by processes described in: Journal of American Chemical Society, Vol. 33, pp1973, 1911; Journal of American Chemical Society, Vol. 65, pp1090, 1943; Journal of American Chemical Society, Vol. 75, pp675, 1953; Chemische Berichte, Vol. 95, pp2885, 1962; Journal of Chemical Society, pp681, 1947; Journal of Chemical Society, pp201, 1948; Journal of Chemical Society, pp354, 1950; and Bulletin de la Societe Chemique de France, pp228, 1949.

The compound (II) used in the above reaction (a) may take the form of a salt. For obtaining larger amounts of the compounds (III) and (IV) than the amount of the compound (V), the compound (II) is generally used in an equivalent amount of 1-2, preferably 1-1.5 for the following reason. That is, the reaction (a) tends to proceed such that the amounts of the compounds (III) and (IV) to be produced are larger than the amount of the compound (V) if the compound (II) is used in an equivalent amount smaller than 2 with respect to the compound (I), and such that the amount of the compound (V) to be produced is larger than the amounts of the compounds (III) and (IV) if the compound (II) is used in an equivalent amount larger than 2 with respect to the compound (I).

The reaction (a) may take place in the presence of an acid receptor, which may be selected from the group consisting of: alkali metal compounds such as sodium hydrogencarbonate, sodium carbonate, potassium carbonate, sodium hydroxide and sodium methoxide; and organic tertiary amines such as pyridine, trimethylamine, triethylamine, diisopropylethylamine, and 4-dimethylaminopyridine. Such acid receptor is used in an equivalent amount of 1–6 with respect to the compound (I).

The reaction (a) is generally effected at a temperature within a range between −30° C. and 150° C., preferably between 0° C. and 120° C., more preferably 0° C. and 80° C. A solvent for the reaction may be selected from the group consisting of: alkanols such as methanol and ethanol; hydrocarbon halides such as dichloromethane and chloroform; aromatic compounds such as benzene, toluene and pyridine; acetonitrile; dimethylformamide; and dimethylsulfoxide.

Among the thus obtained compounds (III), (IV) and (V), the compound (III) is isolated by crystallization or column chromatography. The isolated compound (III) is reacted with a suitable oxidizing agent as described below according to the reaction (b), whereby the desired compound (VI) is obtained.

As the oxidizing agent used in the reaction (b) for oxidizing the compound (III), various known oxidizing agents are employed. For instance, the oxidizing agent may be selected from the group consisting of: organic peroxides such as m-chloroperbenzoic acid, peracetic acid and monoperoxyphthalic acid magnesium salt; and inorganic peroxides such as hydrogen peroxide and sodium periodate. The amount of the oxidizing agent to be used is 1–1.5 times the amount of the compound (III) in molar ratio, preferably 1–1.2 times. A solvent for the reaction may be selected from the group consisting of: hydrocarbon halides such as dichloromethane and chloroform; alkanols such as ethyl alcohol and methyl alcohol; and ethyl acetate. The reaction temperature is in a range between −20° C. and room temperature, preferably between −10° C. and 10° C.

While the process of producing the novel imidazoline derivative according to the present invention has been described, the imidazoline derivative is isolated and purified by crystallization or column chromatography from the reaction mixtures.

The compounds (I), (III) and (VI) produced by the reactions according to the above formula (21) contain tautomers. The reactions of these tautomers to obtain the desired starting compounds or final compounds are effected in substantially the same manner as described above in detail. These reactions are considered to be a part of the process of producing the imidazoline derivative according to the principle of the present invention.

Those tautomers are illustrated in the following formulas (22) through (24). The formulas (22-1) through (22-4) indicate the tautomers of the compound (I). The formulas (23-1) and (23-2) indicate the tautomers of the compound (III). The formulas (24-1) and (24-2) indicate the tautomers of the compound (VI).

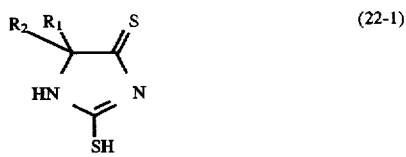

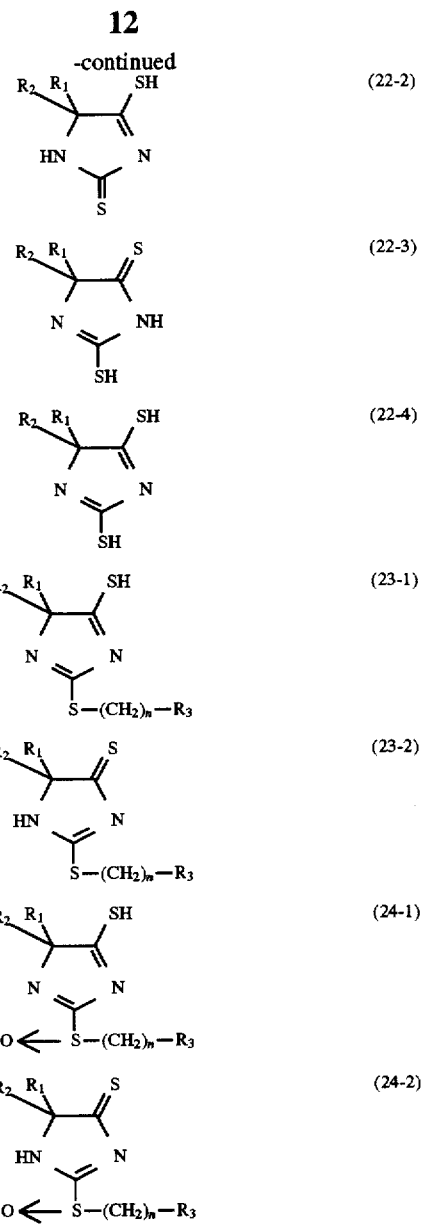

The tautomers of the imidazoline derivative produced according to this invention have respective equilibrium states and respective stable structures.

Detailed analysis of the imidazoline derivative represented by the above formula (13) or possible tautomers thereof according to the present invention revealed that the imidazoline derivative or possible tautomers thereof have an effect of promoting production of a basic Fibroblast Growth Factor (abbreviated as "bFGF") when the imidazoline derivative or the tautomers thereof act on a living subject.

Further, the effect of the imidazoline derivative and possible tautomers thereof according to the present invention on an acetic acid-induced gastric ulcer (as shown in the result of the test of Example 22 which will be described) indicates that the imidazoline derivative and the tautomers thereof have an effect of promoting production of cell growth factors such as an epidermal growth factor (EGF), a platelet-derived growth factor (PDGF) or a hepatocyte growth factor (HGF).

The above-described bFGF was found by Gospodarowicz in 1974 as an activating factor which proliferates the fibroblast in a brain of a calf. A further study of the bFGF revealed that the bFGF is widely distributed in a living body, e.g., in viscera such as brain, hypophysis, heart, liver, yellow body, kidney, adrenal glands, testes, ovary, placenta, prostate, ointment and bone, and in cells such as blood platelet, endothelial cell, leiomyocyte, retinal pigmentary epithelial cell, astroglia, macrophage (monocyte). The bFGF is generally known to have an activity which induces regeneration of blood vessel and differentiation of mesoderm as well as an effect of promoting proliferation of the fibroblast, endothelial cell, leiomyocyte and chondrocyte. In view of these properties, it is expected to employ the bFGF for various kinds of drugs. For instance, it is expected to employ the bFGF for a vulnerary and an anti-ulcer drug in view of its capability to remedy cells which are damaged by wound and ulcer. Since the bFGF has an effect of growth of bones, it is considered to be effective to remedy osteoporosis. Further, the bFGF may be employed for a thrombolytic drug since it has an effect of removing thrombus.

Thus, the bFGF has an excellent physiological activity as described above. The imidazoline derivative or possible tautomers thereof according to the present invention are effective to promote the production of the bFGF. Thus, the imidazoline derivative or possible tautomers thereof of the present invention may act as an effective component of the vulnerary (or anti-ulcer drug) also according to the present invention, osteoporotic remedy and thrombolytic drug as described above. These drugs are formulated in an ordinary process.

The above-described drugs contain, as an effective component, an imidazoline derivative of the present invention or possible tautomers thereof, and also contain suitable additives as needed, such as a binder, an excipient or vehicle, a lubricant, an emulsifier, a disintegrater, a wetting agent, an antiseptics, and a coloring agent, which are used for pharmaceuticals in general. The binder may be selected from among gum arabic, polyvinylpyrrolidone, sorbit, tragacanth and gelatin. The excipient may be selected from among lactose, sugar, sorbit, corn starch, calcium phosphate and glycine. The lubricant may be selected from among magnesium stearate, talc, polyethylene glycol and silica. The disintegrator may be selected from among carboxymethyl cellulose calcium and potato starch. The wetting agent may be selected from among methyl cellulose, aluminum stearate gel, carboxymethylcellulose, gelatin, hydroxyethyl cellulose, hydrogenated edible oil and sorbit syrup. The antiseptics may be sorbic acid or p-hydroxybenzoic acid.

The vulnerary (or anti-ulcer drug) including the imidazoline derivative of the present invention or possible tautomers thereof may take various forms such as tablets, powder, granule, capsules, solution, and parenteral injection. The dose of the vulnerary should be suitably adjusted depending upon the age, weight and wound symptom of the patient and the type of administration of the vulnerary. In the case of oral administration, a suitable dose of the vulnerary for an ordinary adult per day is such that the amount of the imidazoline derivative or possible tautomers thereof as the effective component of the vulnerary is about 1–1000 mg.

Like the vulnerary (anti-ulcer drug), the osteoporotic remedy and thrombolytic drug may take various forms as described just above.

There will be described some examples of the present invention to further clarify the concept of this invention. It is to be understood that the present invention is not limited to the details of these examples.

EXAMPLE 1

Preparation of 2-(2-N-trifluoroacetylaminobenzylsulfinyl)-5,5-dimethylimidazolin-4-thione (a) Initially, 10 g of 5,5-dimethyl-2,4-dithiohydantoin and 17.6 g of 2-N-trifluoroacetylaminobenzylbromide were dissolved in 200 mL of chloroform. The reaction mixture was stirred at the room temperature overnight. The precipitate were filtered, and washed with 200 mL of chloroform and 200 mL of saturated aqueous solution of sodium hydrogencarbonate (NaHCO$_3$). Subsequently, the organic solvent layer was dried over magnesium sulfate (MgSO$_4$), and concentrated in vacuo. The thus obtained residue was recrystallized from dichloromethane-petroleum-ether to give the compound of 2-(2-N-trifluoroacetylaminobenzylthio)-5,5-dimethylimidazolin-4-thione as colorless needles. The yield of this compound was 16.4 g with a yield ratio of 73%, and its melting point was 174°–176° C.

A result of a $^1$H-NMR analysis of the compound is as follows:

$^1$H-NMR (CDCl$_3$, δ, ppm, TMS) 1.35 (6H, s, —CH$_3$×2), 4.20 (2H, s, —CH$_2$—Ar), 7.10–7.80 (4H, m, Ar)

(b) To a solution of 1.5 g of the above obtained 2-(2-N-trifluoroacetylaminobenzylthio)-5,5-dimethylimidazolin-4-thione in 50 mL of chloroform, 0.99 g of m-chloroperbenzoic acid (purity 80%) was added portionwise under ice-cooling and stirring. The mixture was kept to be stirred for 30 minutes to proceed the reaction. The reaction mixture was washed with saturated aqueous solution of sodium hydrogencarbonate (NaHCO$_3$) and then washed with water, dried over magnesium sulfate (MgSO$_4$), and concentrated in vacuo. The residue was purified by column chromatography [developing solvent= CHCl$_3$:MeOH=100:1 (volume ratio, v/v)]. Recrystallization from diethyl ether gave the desired compound of 2-(2-N-trifluoroacetylaminobenzylsulfinyl)-5,5-dimethylimidazolin-4-thione as yellowish needles. The yield of the compound was 0.96 g with a yield ratio of 61.2%, and its melting point was 136°–137° C.

A result of a $^1$H-NMR analysis of the compound is as follows:

$^1$H-NMR (CDCl$_3$, δ, ppm, TMS) 1.32 (6H, s, —CH$_3$×2), 4.08 (2H, s, —CH$_2$—Ar), 7.10–7.80 (4H, m, Ar)

EXAMPLE 2

Preparation of 2-(2-dimethylaminobenzylsulfinyl)-5,5-dimethylimidazolin-4-thione In the above process (a) of the Example 1, 2-dimethylaminobenzylchloride hydrochloride in place of 2-N-trifluoroacetylaminobenzylbromide was reacted following the procedure of Example 1, to obtain the desired compound of 2-(2-dimethylaminobenzylthio)-5,5-dimethylimidazolin-4-thione. To a solution of 10 g of the thus obtained compound in 200 mL of chloroform, 8.1 g of m-chloroperbenzoic acid (purity 80%) was added portionwise under ice-cooling and stirring. The mixture was kept to be stirred for one hour to proceed the reaction. The reaction mixture was washed with saturated aqueous solution of sodium hydrogencarbonate (NaHCO$_3$) and then washed with water, dried over magnesium sulfate (MgSO$_4$), and concentrated in vacuo. The residue was purified by column chromatography [developing solvent=CHCl$_3$:MeOH=100:1 (volume ratio, v/v)]. Recrystallization from diethyl ether gave the desired compound of 2-(2-dimethylaminobenzylsulfinyl)-5,5-dimethylimidazolin-4-thione as yellowish needles. The yield of the compound was 7.6 g with a yield ratio of 72.3%, and its melting point was 103°–106° C.

A result of a ¹H-NMR analysis of the compound is as follows:

¹H-NMR (CDCl$_3$, δ, ppm, TMS) 1.45 (6H, s, —CH$_3$×2), 2.71 {6H, s, —N(CH$_3$)$_2$}, 4.45 (2H, s, —CH$_2$—Ar), 7.07~7.50(4H, m, Ar), 7.80 (1H, br s, NH)

EXAMPLE 3

Preparation of 2-(2-N-formyl-N-methylaminobenzylsulfinyl)-5,5-dimethylimidazolin-4-thione Initially, in the process (a) of the Example 1, 2-N-formyl-N-methylaminobenzylbromide in place of 2-N-trifluoroacetylaminobenzylbromide was reacted following the procedure of Example 1, to obtain the compound of 2-(2-N-formyl-N-methylaminobenzylthio)-5,5-dimethylimidazolin-4-thione. To a solution of 4.5 g of the thus obtained compound in 100 mL of chloroform, 3.2 g of m-chloroperbenzoic acid (purity 80%) was added portionwise under ice-cooling and stirring. The mixture was kept to be stirred for one hour to proceed the rection. The reaction mixture was washed with saturated aqueous solution of sodium hydrogencarbonate (NaHCO$_3$) and then washed with water, dried over magnesium sulfate (MgSO$_4$), and concentrated in vacuo. The residue was purified by column chromatography [developing solvent=CHCl$_3$:MeOH=50:1 (volume ratio, v/v)]. Recrystallization from diethyl ether gave the desired compound of 2-(2-N-formyl-N-methylaminobenzylsulfinyl)-5,5-dimethylimidazolin-4-thione as yellowish needles. The yield of the compound was 4.34 g with a yield ratio of 91.7%, and its melting point was 115°–117° C.

A result of a ¹H-NMR analysis of the compound is as follows:

¹H-NMR (CDCl$_3$, δ, ppm, TMS) 1.43 (6H, s, —CH$_3$×2), 3.27 (3H, s, —NCH$_3$), 4.36 (2H, s, —CH$_2$—Ar), 7.07~7.83 (4H, m, Ar), 8.23 (1H, s, —CHO), 11.10 (1H, br s, NH)

EXAMPLE 4

Preparation of 2-(8-quinolinylmethylsulfinyl)-5,5-dimethylimidazolin-4-thione

Initially, in the process (a) of the Example 1, 8-bromomethylquinolin in place of 2-N-trifluoroacetylaminobenzylbromide was reacted following the procedure of Example 1, to obtain the compound of 2-(8-quinolinylmethylthio)-5,5-dimethylimidazolin-4-thione. To a solution of 1 g of the thus obtained compound in 50 mL of chloroform, 0.72 g of m-chloroperbenzoic acid (purity 80%) was added portionwise under ice-cooling and stirring. The mixture was kept to be stirred for one hour to proceed the reaction. The reaction mixture was washed with saturated aqueous solution of sodium hydrogencarbonate (NaHCO$_3$) and then washed with water, dried over magnesium sulfate (MgSO$_4$), and concentrated in vacuo. The residue was purified by column chromatography [developing solvent=CHCl$_3$:MeOH=100:1 (volume ratio, v/v)]. Recrystallization from chloromethane-diethyl ether gave the desired compound of 2-(8-quinolinylmethylsulfinyl)-5,5-dimethylimidazolin-4-thione as yellowish needles. The yield of the compound was 0.73 g with a yield ratio of 69.3%, and its melting point was 131°–133° C.

A result of a ¹H-NMR analysis of the compound is as follows:

¹H-NMR (DMSO-d$_6$, δ, ppm, TMS) 1.47 (6H, s, —CH$_3$× 2), 5.05 (2H, s, —CH$_2$—Ar), 7.40~9.15(6H, m, Ar)

EXAMPLE 5

Preparation of 2-(2-N-trifluoroacetyl-N-methylaminobenzylsulfinyl)-5,5-dimethylimidazolin-4-thione Initially, in the process (a) of the Example 1, 2-N-trifluoroacetyl-N-methylaminobenzylbromide in place of 2-N-trifluoroacetylaminobenzylbromide was reacted following the procedure of Example 1, to obtain the compound of 2-(2-N-trifluoroacetyl-N-methylaminobenzylthio)-5,5-dimethylimidazolin-4-thione. To a solution of 1.5 g of the thus obtained compound in 100 mL of chloroform, 0.95 g of m-chloroperbenzoic acid (purity 80%) was added portionwise under ice-cooling and stirring. The mixture was kept to be stirred for 30 minutes to proceed the reaction. The reaction mixture was washed with saturated aqueous solution of sodium hydrogencarbonate (NaHCO$_3$) and then washed with water, dried over magnesium sulfate (MgSO$_4$), and concentrated in vacuo. The residue was purified by column chromatography [developing solvent= CHCl$_3$:MeOH=100:1 (volume ratio, v/v)]. Recrystallization from diethyl ether gave the desired compound of 2-(2-N-trifluoroacetyl-N-methylaminobenzylsulfinyl)-5,5-dimethylimidazolin-4-thione as yellowish needles. The yield of the compound was 1.13 g with a yield ratio of 72.3%, and its melting point was 122°–123° C.

A result of a ¹H-NMR analysis of the compound is as follows:

¹H-NMR (CDCl$_3$, δ, ppm, TMS) 1.38 (6H, s, —CH$_3$×2), 3.30 (3H, s, —NCH$_3$), 4.37 (2H, s, —CH$_2$—Ar), 7.10~7.77 (4H, m, Ar)

In the following Examples 6–16, the desired compounds were prepared using appropriate starting compounds, in the same manner as in Example 1. The yield ratio, melting point and ¹H-NMR analysis result of each of these compounds are indicated below.

EXAMPLE 6

Preparation of 2-(2-dimethylaminobenzylsulfinyl)-5-phenyl-5-methylimidazolin-4-thione Yield ratio: 62.3% Melting point: 64°–66° C. ¹H-NMR (CDCl$_3$, δ, ppm, TMS) 1.81 (3H, s, —CH$_3$), 2.63 {6H, s, —N(CH$_3$)$_2$}, 4.48 (2H, s, —CH$_2$—Ar), 7.01~7.63 (9H, m, Ar)

EXAMPLE 7

Preparation of 2-(2-dimethylaminobenzylsulfinyl)-5,5-diethylimidazolin-4-thione

Yield ratio: 72.1% Melting point: 90°–91° C. ¹H-NMR (CDCl$_3$, δ, ppm, TMS) 0.73 (6H, s, —CH$_2$CH$_3$×2), 1.43~2.03 (4H, m, —CH$_2$CH$_3$×2), 2.72 {6H, s, —N(CH$_3$)$_2$}, 4.46 (2H, s, —CH$_2$—Ar), 7.06~7.59 (4H, m, Ar)

EXAMPLE 8

Preparation of 2-(2-dimethylamino-5-methylbenzylsulfinyl)-5,5-dimethylimidazolin-4-thione Yield ratio: 34.8% Melting point:—(amorphous) ¹H-NMR (CDCl$_3$, δ, ppm, TMS) 1.46 (6H, s, —CH$_3$×2), 2.03 (3H, s, —ArCH$_3$), 2.70 {6H, s, —N(CH$_3$)$_2$}, 4.37 (2H, s, —CH$_2$—Ar), 7.03~7.28 (3H, m, Ar)

EXAMPLE 9

Preparation of 2-(2-dimethylamino-5-methoxybenzylsulfinyl)-5,5-dimethylimidazolin-4-thione Yield ratio: 35.6% Melting point:—(amorphous) ¹H-NMR (CDCl$_3$, δ, ppm, TMS) 1.47 (6H, s, —CH$_3$×2), 2.69 {6H, s, —N(CH$_3$)$_2$}, 3.79 (3H, s, —OCH$_3$), 4.46 (2H, s, —CH$_2$—Ar), 6.70~7.39 (3H, m, Ar)

EXAMPLE 10

Preparation of 2-(2-dimethylamino-4-fluorobenzylsulfinyl)-5,5-dimethtylimidazolin-4-thione Yield ratio: 22.3% Melting point:—(amorphous) $^1$H-NMR (CDCl$_3$, δ, ppm, TMS) 1.53 (6H, s, —CH$_3$×2), 2.68 {6H, s, —N(CH$_3$)$_2$}, 4.46 (2H, s, —CH$_2$—Ar), 6.67~7.42 (3H, m, Ar)

EXAMPLE 11

Preparation of 2-[2-N-(2,2,2-trifluoroethyl)-N-methylaminobenzylsulfinyl]-5,5-dimethylimidazolin-4-thione Yield ratio: 38.6% Melting point:—(amorphous) $^1$H-NMR (CDCl$_3$, δ, ppm, TMS) 1.45 (6H, s, —CH$_3$×2), 2.86 (3H, t, —NCH$_3$), 3.53 (2H, q, —CH$_2$CF$_3$), 4.60 (2H, s, —CH$_2$—Ar), 7.02~7.52 (4H, m, Ar)

EXAMPLE 12

Preparation of 2-[2-N-(2,2,2-trifluoroethyl)aminobenzylsulfinyl]-5,5-dimethylimidazolin-4-thione Yield ratio: 67.5% Melting point: 90°–92° C. $^1$H-NMR (CDCl$_3$, δ, ppm, TMS) 1.44 (6H, s, —CH$_3$×2), 3.88 (2H, q, —CH$_2$CF$_3$), 4.47 (2H, s, —CH$_2$—Ar), 6.63~7.23 (4H, m, Ar)

EXAMPLE 13

Preparation of 2-(2-N-cyclopropylmethyl-N-methylaminobenzylsulfinyl)-5,5-dimethylimidazolin-4-thione Yield ratio: 49.3% Melting point: 95°–97° C. $^1$H-NMR (CDCl$_3$, δ, ppm, TMS) 0.07~1.00 {5H, m, —CH(CH$_2$)$_2$}, 1.49 (6H, s, —CH$_3$×2), 2.73~2.87 (5H, m, —NCH$_3$+—NCH$_2$—), 4.52 (2H, s, —CH$_2$—Ar), 7.08~7.58 (4H, m, Ar)

EXAMPLE 14

Preparation of 2-(2-N-isobutyl-N-methylaminobenzylsulfinyl)-5,5-dimethylimidazolin-4-thione Yield ratio: 60.1% Melting point: 99°–101° C. $^1$H-NMR (CDCl$_3$, δ, ppm, TMS) 0.95 {6H, d, —CH(CH$_3$)$_2$}, 1.47 (6H, s, —CH$_3$×2), 2.67 (5H, m, —NCH$_3$+—NCH$_2$—), 4.57 (2H, s, —CH$_2$—Ar), 6.83~7.67 (4H, m, Ar), 9.23 (1H, br s, NH)

EXAMPLE 15

Preparation of 2-(2-N-ethyl-N-methylaminobenzylsulfinyl)-5,5-dimethylimidazolin-4-thione Yield ratio: 82.3% Melting point: 87°–89° C. $^1$H-NMR (CDCl$_3$, δ, ppm, TMS) 1.12 (3H, t, —NCH$_2$CH$_3$), 1.47 (6H, s, —CH$_3$×2), 2.68 (3H, s, —NCH$_3$), 2.95 (2H, q, —NCH$_2$CH$_3$), 4.47 (2H, s, —CH$_2$—Ar), 6.93~7.60 (4H, m, Ar), 10.78 (1H, br s, NH)

EXAMPLE 16

Preparation of 2-(2-dimethylaminobenzylsulfinyl)-5-ethyl-5-methylimidazolin-4-thione Yield ratio: 85.7% Melting point: 79°–82° C. $^1$H-NMR (CDCl$_3$, δ, ppm, TMS) 0.73 (3H, t, —CH$_2$CH$_3$), 1.45 (3H, s, —CH$_3$), 1.53 (2H, q, —CH$_2$CH$_3$), 2.73 {6H, s, —N(CH$_3$)$_2$}, 4.50 (2H, s, —CH$_2$—Ar), 6.83~7.63 (4H, m, Ar), 10.23 (1H, br s, NH)

EXAMPLE 17

Effect of imidazoline derivatives on the additional expression of the bFGF

There will be next explained an effect of the imidazoline derivatives in vitro.

Initially, there will be explained an effect of the imidazoline derivative on the additional expression of bFGF in the cells cultured. The reverse transcription-polymerase chain reaction (PCR) was used to explain the effects of imidazoline derivatives on the additional expression of bFGF, and then the PCR products were subjected to electrophoresis to confirm a bFGF band.

An established rat gastric mucosal epithelial cell line RGM1 was seeded in petri dishes (1×10$^6$cells/dish), in the presence of D-MEM/Ham 12 (1:1) mixed medium containing 20% fetal calf serum. After 24 hours, the imidazoline derivatives as the specimen drugs according to the present invention were applied in the culture medium, and the cells were cultured for 48 hours. The compounds prepared in Examples 1 and 14 were used as the specimen drugs. Cultures were then supplemented with the compounds in final concentrations (10 μM and 100 μM for the compound of Example 1, and 3 μM, 10 μM and 100 μM for the compound of Example 14).

From the cultured cells of each sample subjected to the above-described processing by the specimen drugs, total cellular RNA was extracted according to Acid Guanidinium Thiocyanate-Phenol-Chloroform method (AGPC). Described more specifically, after cultivation with the above compounds in the culture medium, the culture supernatant was completely removed by suction. To the cells of each sample left in the petri dish, 500 μL of Solution D (consisting of: 4M of guanidinethiocyanate; 25 mM of sodium citrate; 0.5% sarkosyl solution, 0.1M of 2-mercaptoethanol) was added, and the cells were scraped with rubber policeman (available from SUMITOMO BAKELITE CO., LTD.). The thus obtained cell suspension was transfered into a micro centrifuge tube, and there were successively added 50 μL of 2M sodium acetate (pH 4.0), 500 μL of water-saturated phenol and 100 μL of chloroform-isoamyl alcohol (49:1). The suspension was mixed each time the above-described substances were added. The suspension was placed on ice for 15 minutes after it was intensely shaken for 1 minute. Then, the suspension was centrifuged at 10000 rpm for 20 minutes at 4° C. The aqueous layer (upper layer) was transfered into another micro centrifuge tube, and was intimately mixed with an equivalent amount of isopropanol. After the mixture was kept at –20° C. for one hour, it was centrifuged at 10000 rpm for 20 minutes at 4° C. After the centrifugation, the upper layer was discarded, and a precipitate of mRNA was completely dissolved in 200 μL of Solution D. The thus obtained solution was mixed again with an equivalent amount of isopropanol and the mixture was kept at –20° C. for one hour. The mixture was then subjected to centrifugation for 20 minutes at 4° C. and 10000 rpm. After the centrifugation, the supernatant was discarded, and the precipitate was centrifuged at 10000 rpm for 10 minutes at 4° C. The supernatant was discarded, while the precipitate was dried in vacuo for 5 minutes. The total RNA was dissolved in 50 μL of distilled water processed by diethyl pyrocarbonate (DEPC). The concentration of total RNA was measured on the basis of its absorbance at 260 nm by ultraviolet spectrum.

The CDNA synthesis was performed by means of Reverse Transcriptase using the above obtained total RNA as a template. As a primer, a random primer was employed. Initially, 13.1 μL of a mixture of the extracted total RNA and the random primer was heated at 95° C. for five minutes, so that the total RNA was denatured. After the mixture was rapidly cooled on ice, there were added 5 µL of 5×First Strand Buffer [consisting of: 250 mM Tris-HCl (pH 8.3); 375 mM KCl; and 15 mM $MgCl_2$], 2.5 µL of 0.1M DTT (dithiothreitol), 0.7 µL of 28000 U/mL RNasin, 3.5 µL of 4 mM 4 dNTP (nucleoside triphosphate) and 0.2 µL of 200 U/µL RT. The mixture having a total volume of 25 µL was incubated at 37° C. for 90 minutes. The reaction was terminated after the mixture was held at 95° C. for 5 minutes.

The thus obtained CDNA was subjected to the PCR method so as to amplify a bFGF CDNA. Initially, there was prepared a solution of 1 µL of 10×PCR Buffer [consisting of 100 mM Tris-HCl (pH 8.3), 500 mM KCl and 15 mM $MgCl_2$], 0.5 µL of 4 mM 4 dNTP, 0.05 µL of 5 U/µL Taq polymerase and 5 µL of a mixed solution of two kinds of synthesized primers on 5' and 3' sides which are each specific to the rat bFGF CDNA. To the thus prepared mixed solution, the above obtained cDNA was added, and the solution was covered with 20 µL of mineral oil. The solution was left for reaction using DNA thermal cycler PJ20000 (available from PERKIN ELMER), under the following conditions: thermal denaturation for 1 minute at 94° C.; annealing for 1 minute at 55° C.; and extension reaction for 2 minutes at 72° C. The reaction was performed in 30 cycles. After the reaction was terminated, the mineral oil was removed from the solution, and the PCR products were subjected to agarose gel electophoresis to confirm a band of the bFGF. The degree of luminecense of the band of the bFGF in the cells with imidazloline derivatives of each sample was compared with that of a band of bFGF in cells without the imidazoline derivatives. The result is indicated in TABLE 1, wherein "++" indicates that the expression of the bFGF mRNA in the imidazoline-treated cells was considerably increased, while "+" indicates the expression of the bFGF mRNA was increased to some extent.

TABLE 1

| Drugs (Examples) | Concentration (µM) | Band Intensity |
| --- | --- | --- |
| 1 | 10 | + |
|  | 100 | + |
| 14 | 3 | ++ |
|  | 10 | ++ |
|  | 100 | ++ |

In the experiment as described above, the DNA if used in an extremely small amount may be lost with the DNA attached to the experiment instruments during the process of the experiment. In this case, the result of the experiment may be pseudonegative or inaccurate. In view of this, a control experiment was performed by using a primer of β-actine in the same manner as in the above experiment. The result of the control experiment showed that, in each comparative sample of cells, the same band intensity as obtained in the above experiment was obtained. Thus, it was confirmed that the amount of the cDNA used in the above experiment was the same in all samples of the cells, with the same band intensity, without fluctuating factors being caused during the process of the experiment.

It will be recognized from the above TABLE 1 that the imidazoline derivatives of the present invention which act on the cells have an effect of promoting the expression of bFGF mRNA. In general, the amount of the mRNA is proportional to the amount of protein which is coded by the mRNA. Thus, it will be understood that the imidazoline derivative according to the present invention promotes the production of the bFGF.

EXAMPLE 18

Effect of imidazoline derivatives on the additional expression of bFGF

The effect of promoting the production of the bFGF exhibited by the imidazoline derivative of the present invention was confirmed by Enzyme-Linked Immunosorbent Assay (ELISA) method, as described below.

Initially, RGM1 cells which are derived from a gastric mucosa epithelial cell of a Wistar rat were seeded into 24 well plates ($2×10^4$ cells/dish, 1 mL/well), and cultured for 24 hours. As the imidazoline derivative according to the present invention, the compound obtained in Example 14 was used. The compound was applied to the cells in final concentrations of 3 µM, 10 µM and 30 µM. After 24 hours, the culture supernatants which correspond to the respective concentration values were collected, and analyzed using bFGF ELISA kit. Similarly, the culture supernatants were collected 48 hours after the application of the compound. Described more specifically, 50 µL of each culture supernatant was applied to a 96 well microplate coated with bFGF monoclonal antibody. The plate was incubated for a predetermined time so that the bFGF contained in each culture supernatant was bonded to the bFGF monoclonal antibody. Thereafter, each supernatant was reacted with horseradish peroxidase conjugated antibody which is able to recognize another epitope of the bFGF, so as to form, on the 96 well microplate, a sandwich type composite body consisting of immobilized antibody (bFGF monoclonal antibody), antigen (bFGF), and HRP linked antibody. Subsequently, HRP linked antibody of the composite body was colored using o-phenylenediamine and $H_2O_2$. The reaction was terminated by using sulfuric acid after a predetermined time has elapsed. Then, the absorbance of reactant at 490 nm was measured using a micro-platereader. The production amount of the bFGF was obtained for each culture supernatant, on the basis of the measured absorbance values, according to a standard curve prepared for a standard bFGF of a human body.

TABLE 2

| Concentration of drug (µL) | Production amount of bFGF (pg/mL) |
| --- | --- |
| 3 | 15 |
| 10 | 29 |
| 30 | 36 |

It will be understood from the result of Example 18 that the imidazoline derivative according to the present invention advantageously promotes the production of the bFGF and that the amount of the bFGF to be produced depends on the concentration of the imidazoline derivatives

EXAMPLE 19

Inhibitory effect on water-immersion restraint stress-induced gastric ulcer

Male 7-week SD rats were fasted for 24 hours, with a fast of water beginning in early morning of the day when the experiments were performed. The rats were classified into groups each consisting of five rats, such that all the groups have substantially the same average weight. Thirty minutes before giving a stress to the rats, the compounds of the Examples indicated in TABLE 3 were orally administered as specimen drugs to the rats, with a dose of 10 mg/kg. The rats were then kept in stress cages, and were given a stress by immersing the cages in a water bath kept at a substantially constant temperature of 23°±1° C., such that the water level was at the height of the xiphoid of the rats. Seven hours later, the specimen rats were sacrificed by ether, and the gastric mucosa of each rat was semi-fixed with 2% formaline. The longitudinal length of the damaged area of the gastric mucosa was measured. A sum of the measured length values of the rats of each group was calculated as an ulcer index. An anti-ulcer or ulcer inhibitory percent (%) was calculated as {1−(ulcer index of each group of specimen rats)/(ulcer index of non-specimen group)}×100. The ulcer inhibitory percent values corresponding to the individual specimen drugs are indicated in TABLE 3.

TABLE 3

| Drug (Examples) | Dose (mg/kg) | Inhibitory Percent (%) |
| --- | --- | --- |
| 7 | 10 | 53.9 |
| 12 | 10 | 46.6 |
| 15 | 10 | 99.9 |

EXAMPLE 20

Inhibitory effect on hydrochloric acid-ethanol-induced gastric ulcer

Male SD rats of 7-week age were fasted for 24 hours, with a fast of water beginning in early morning of the day when the experiments were performed. The rats were classified into groups each consisting of five rats, such that all the groups have substantially the same average weight. Before giving hydrochloric acid-ethanol to the rats, the compounds of the Examples indicated in TABLE 4 were orally administered as specimen drugs to the rats, with a dose of 30 mg/kg. Thirty minutes later, 1 mL of 98% ethanol containing 200 mM of hydrochloric acid was orally administered to each specimen rat. One hour later, the specimen rats were sacrificed by ether, and the gastric mucosa of each rat was semi-fixed with 2% formalin. The longitudinal length of the damaged area of the gastric mucosa was measured, and the anti-ulcer percent values of the individual specimen drugs were calculated on the basis of the sum of the measured length values of each group of the specimen rats, in the same manner as in Example 19. The calculated ulcer inhibitory percent values are indicated in TABLE 4.

TABLE 4

| Drug (Examples) | Dose (mg/kg) | Inhibitory Percent (%) |
| --- | --- | --- |
| 4 | 30 | 90.3 |
| 15 | 30 | 97.4 |
| 16 | 30 | 98.6 |

EXAMPLE 21

Inhibitory effect on indomethacin-induced gastric ulcer

Male SD rats of 7-week age were fasted for 24 hours, with a fast of water beginning in early morning of the day when the experiments were performed. The rats were classified into groups each consisting of eight rats, such that all the groups have substantially the same average weight. Before giving indomethacine to the rats, the compounds of the Examples indicated in TABLE 5 were orally administered as specimen drugs to the rats, with a dose of 30 mg/kg. Thirty minutes later, indomethacin was orally administered to each specimen rat, with a dose of 25 mg/kg (1 mL/rat). Seven hours later, the specimen rats were sacrificed by ether, and the gastric mucosa of each rat was semi-fixed with 2% formalin. The longitudinal length of the damaged area of gastric mucosa was measured, and the anti-ulcer percent values of the individual specimen drugs were calculated on the basis of the sum of the measured length values of each group of specimen rats, in the same manner as in EXAMPLE 19. The calculated ulcer inhibitory percent values are indicated in TABLE 5.

TABLE 5

| Drug (Examples) | Dose (mg/kg) | Inhibitory Percent (%) |
| --- | --- | --- |
| 2 | 30 | 100 |
| 15 | 30 | 99.2 |
| 16 | 30 | 97.2 |

It will be understood from the result of the tests in Examples 19–21 that the compounds according to the present invention exhibited excellent effects of inhibiting the ulcer formation.

EXAMPLE 22

Healing effect on acetic acid-induced gastric ulcer of rat

A male Donryu rat of 7-week age was subjected to abdominal incision to expose the stomach, with pentobarbital used as an anesthesia. Using a metal ring having an inside diameter of 10 mm, 200 μL of glacial acetic acid was applied, for 60 seconds, with a serosa-side of a boundary area between the antrum and the corps. The abdomen of the specimen rat subjected to the glacial acetic acid was closed by an operation, and the rat was then fed in a normal way. The compound prepared in Example 2, that is, 2-(2-dimethylaminobenzylsulfinyl)-5,5-dimethylimidazoline-4-thione was used as the specimen drug. This compound was orally administered to the specimen rat two times a day (at 9:00 a.m. and 5:00 p.m.), each time with a dose of 25 mg/kg, beginning on the day following the day on which the glacial acetic acid was applied to the rat. The oral administration continued for 10 consecutive days, with a total of 20 administrations. On the day following the last day of the administration, the specimen rat was sacrificed by ether, and the ulcer portion of the rat was semi-fixed with formalin. The surface area of the ulcer portion was measured. The healing percent (%) calculated on the basis of the measured surface area was 40.8%.

It will be understood from the result of the test in Example 22 that the compounds according to the present invention exhibited excellent effects of promoting the healing of ulcers.

EXAMPLE 23

Inhibitory effect on the gastric acid secretion in a pylorus ligated rat

Male 7-week SD rats were fasted for 24 hours, with a fast of water beginning in early morning of the day when the experiments were performed. The rats were classified into groups each consisting of five rats, such that all the groups have substantially the same average weight. The experiments were performed according to a method of Shay et. al. (Shay, H. et. al., Gastroenterology, Vol. 5, pp43, 1945). Described more specifically, each of the rats was subjected to a light anesthesia by ether, and the hair of the abdomen of each rat was clipped. Then, the abdomen was incised over a length of 1.5 cm along the center line downwards from a portion 1 cm below the xiphoid of the rat, and the stomach was taken out of the body. A portion connecting the pylorus and the duodenum was ligated by suturing thread. As specimen drugs, the compounds of Examples indicated in TABLE 6 were used with different doses also indicated in TABLE 6. Each of the compounds was prepared as a liquid medicine, and administered within the intestinum duodenum of the rat in an amount of 0.2 mL per 100 g of the weight of the rat immediately after the ligation. After the administration, the skin of the abdominal muscle and abdomen was sutured. The rats were kept in cages and fasted for 4 hours with a fast of water. Then, the rats were sacrificed by ether, and the stomach of each rat was removed. The gastric content was obtained from a small hole formed through the stomach of each rat and was collected in a test tube. The collected gastric content was subjected to centrifugation under 3000 rpm for 10 minutes, so as to precipitate solid matters. An amount of supernatant was measured as a volume of gastric acid, and a total acidity of the gastric acid was also measured. A volume of gastric acid inhibitory percent (%) and a total acidity inhibitory percent (%) were calculated in the same manner as the ulcer inhibitory percent was calculated. The results are shown in TABLE 6. The total acidity was obtained as a product of the amount of gastric acid secreted for 4 hours and the acidity per 1 mL of the gastric acid which was subjected to neutralization titration by an aqueous solution of 0.01N sodium hydroxide.

TABLE 6

| | Drug | Dose (mg/kg) | Volume of Gastric acid Inhibitory percent (%) | Total acidity Inhibitory percent (%) |
|---|---|---|---|---|
| Present Invention | Example 15 | 10 | 60.1 | 91.3 |
| | Example 16 | 10 | 41.6 | 77.4 |
| Comparative Example | cimetidine | 10 | 22.7 | 27.7 |
| | | 30 | 31.2 | 51.8 |
| | | 100 | 52.8 | 76.1 |

As can be understood from the results as shown in TABLE 6, the imidazoline derivative of the present invention is effective to inhibit the gastric acid secretion while keeping the total acidity at relatively low levels. The use of the imidazoline derivative of the present invention with a dose of 10 mg/kg provides substantially the same inhibitory effect as obtained by the use of the conventional drug (cimetidine) with a dose of 100 mg/kg. Thus, the use of the imidazoline derivative with a dose which is about one tenth of that of the conventional drug assures excellent inhibitory effects of the gastric acid secretion and total acidity.

EXAMPLE 24

Healing Effect on wound in rat

Male 7-week SD rats were classified into groups each consisting of 6–7 rats, such that all the groups have substantially the same average weight. The experiment was performed on the rats according to a method of Tsurumi et al. (Oyo Yakuri, Vol. 7, pp833, 1973). Initially, the rats were subjected to an anesthesia with pentobarbital. The hair of the back of each rat was clipped, and the skin was disinfected with 70% ethanol. Then, the skin was lightly pulled and punched off in a direction from the right to the left by means of a punch whose diameter is 10 mm, so as to form two open wounds on portions of the back of the rat which are symmetrical to each other with respect to the center line of the back. The compounds of Examples indicated in the following TABLES 7 and 8 were used as specimen drugs, and orally administered once a day to each of the rats with doses indicated in the TABLES 7 and 8. The oral administration continued for 15 consecutive days, beginning from the first day when the wounds were formed on the back of each rat.

To clarify the healing effect on the wounds, an Healing Index and healing days were obtained in the following manner. Initially, the lengths of a major axis and a minor axis of each wound formed on the back were measured using calipers. On the basis of the measured length values, the area of each wound was calculated as the area of an ellipse. The Healing Index was obtained according to a method of Nakano et al. (Oyo Yakuri, Vol. 47, pp29, 1994). Described more specifically, a ratio of area of each wound was chronologically represented in a graph, and an area of the lower part of a curve in the graph during a period from the fifth day to the fifteenth day after the wounds were formed was obtained as the Healing Index. A period from the first day to the fourth day was excluded since this period is an irregular, unstable period in the process of healing of the wound, during which the area of the wound is gradually reduced (Dunphy and Udupa, NEW ENGLAND JOURNAL OF MEDICINE, Vol. 253, pp.847, 1955; Numamoto et al., KISO TO RINSHO, Vol. 8, pp.4027, 1974). The healing days were obtained as the number of the days that were required for the wounds to be completely covered with regenerated epidermises. As for the wound that was healed in more than 15 days, the healing days were obtained as 16 days. The results are also shown in TABLES 7 and 8.

TABLE 7

| Drug (Examples) | Dose (mg/kg) | Healing Index | Healing days |
|---|---|---|---|
| Control | — | 188.3 ± 18.2 | 15.1 ± 0.22 |
| 1 | 50 | 183.2 ± 11.2 | 14.4 ± 0.38 |
| 1 | 100 | 157.5 ± 18.9 | 14.2 ± 0.37* |
| 2 | 50 | 153.0 ± 13.2 | 13.8 ± 0.39* |
| 2 | 100 | 146.7 ± 12.4* | 14.6 ± 0.44 |

*A significant difference was recognized by statistical method (Student's t-test).

TABLE 8

| Drug (Examples) | Dose (mg/kg) | Healing Index | Healing days |
|---|---|---|---|
| Control | — | 152.0 ± 9.5 | 14.3 ± 0.37 |
| 14 | 50 | 116.5 ± 7.0* | 13.5 ± 0.42 |
| 14 | 100 | 126.5 ± 8.3* | 13.6 ± 0.44 |

*A significant difference was recognized by statistical method (Student's t-test).

As can be understood from the results as shown in TABLES 7 and 8, the compounds of Examples 1, 2 and 14 are effective to reduce the healing days and lower the Healing Index. Thus, it is confirmed that the compounds of the present invention can be effectively used as the vulnerary.

EXAMPLE 25

Single-dose toxicity study

Ten male ddY mice (each having a weight of 22–28 g were used as specimen animal in a cage kept at a substantially constant temperature of 23°±1° C. and under a substantially constant humidity of 55±5%. The compound prepared in Example 2, that is, 2-(2-dimethylaminobenzylsulfinyl)-5,5-dimethylimidazoline-4-thione was used as the specimen drug. This compound was suspended in 2% solution of polysorbate 80, and the suspension was administered to each specimen mouse, with different doses. The specimen mice were observed for two weeks after the administration. On the basis of the death percent, lethal dose ($LD_{50}$) which causes a 50% death was obtained as an index indicative of the single dose toxicity. The obtained $LD_{50}$ (oral administration) was 952 mg/kg (95% confidence limits: 791–1138 mg/kg). It was thus confirmed that the $LD_{50}$ (oral administration) of the compound according to the present invention was sufficiently large, indicating a low degree of toxicity or a high degree of safety.

Referring to the following examples, there will be illustrated some examples of drugs which include, as an effective component, the imidazoline derivative according to the present invention. It is noted that these drugs are prepared in various known manners, in various forms which include those other than illustrated below.

EXAMPLE 26

Vulnerary (tablet)

The drug is prepared in an ordinary manner such that each tablet (200 mg) contains the following components:
Effective component (Compound in each Example) ... 30 mg Lactose ... 103 mg Corn starch ... 50 mg Magnesium stearate ... 2 mg Hydroxypropyl cellulose ... 15 mg

EXAMPLE 27

Vulnerary (capsule)

The drug is prepared in an ordinary manner such that each gelatin capsule (340 mg) contains contains the following components:
Effective component (Compound in each Example) ... 30 mg Lactose ... 20 mg Corn starch ... 70 mg Polyvinylpyrrolidone ... 5 mg Crystalline cellulose ... 35 mg

EXAMPLE 28

Vulnerary (granule)

The drug is prepared in an ordinary manner such that 1 g of granule contains the following components:
Effective component (Compound in each Example) ... 100 mg Lactose ... 550 mg Corn starch ... 300 mg Hydroxypropyl cellulose ... 50 mg It will be understood that the imidazoline derivative as represented by the above formula 13 or 15 is a novel compound which has an effect of promoting the production of the bFGF. Therefore, the compound according to the present invention is employed as the anti-ulcer drug, vulnerary, osteoporotic remedy, thrombolytic drug and others. According to the process of producing the imidazoline derivative, the novel compound having excellent effects as indicated above can be advantageously produced.

What is claimed is:

1. An imidazoline derivative or tautomer thereof, which is represented by the following formula (1),

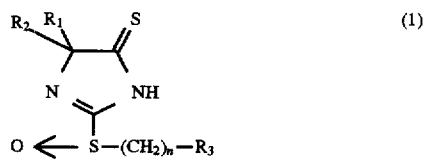

wherein n represents an integer from 1 to 4, and $R_1$ and $R_2$ represent a same one or respective different ones of a hydrogen atom, a lower alkyl group, a phenyl group, and a benzyl group, or in combination represent one of an alkylene group having 2–6 carbon atoms, an alkylidene group having 2–5 carbon atoms and a benzylidene or cinnamylidene group, while $R_3$ represents a phenyl group represented by the following formula (2),

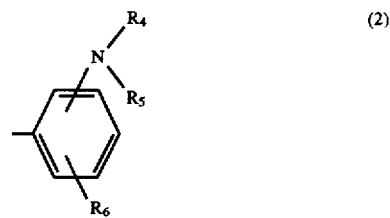

wherein $R_4$ and $R_5$ represent a same one or respective different ones of a hydrogen atom, a lower alkyl group, a lower alkyl group substituted with at least one halogen atom or at least one hydroxyl group, a cycloalkylalkyl group, a lower alkenyl group, a lower alkanoyl group, a lower alkanoyl group substituted with at least one halogen atom, a lower alkoxyalkyl group, a lower alkoxycarbonyl group, a benzoyl group, a benzyloxycarbonyl group, a lower alkylaminocarbonyl group, a lower alkylsulfonyl group, a benzenesulfonyl group and a toluenesulfonyl group, while $R_6$ represents one of a hydrogen atom, a hydroxyl group, a halogen atom, a lower alkyl group, a lower alkoxy group and a nitro group.

2. An imidazoline derivative or tautomer thereof according to claim 1, wherein said formula (1) represents 2-(2-N-trifluoroacetylaminobenzylsulfinyl)-5,5-dimethylimidazolin-4-thione.

3. An imidazoline derivative or tautomer thereof according to claim 1, wherein said formula (1) represents 2-(2-dimethylaminobenzylsulfinyl)-5,5-dimethylimidazolin-4-thione.

4. An imidazoline derivative or tautomer thereof according to claim 1, wherein said formula (1) represents 2-(2-N-isobutyl-N-methylaminobenzylsulfinyl)-5,5-dimethylimidazolin-4-thione.

5. An imidazoline derivative or tautomer thereof according to claim 1, wherein said tautomer of said imidazoline derivative is represented by one of the following formulas (3-1) and (3-2),

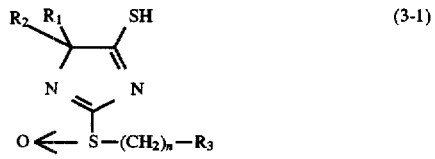

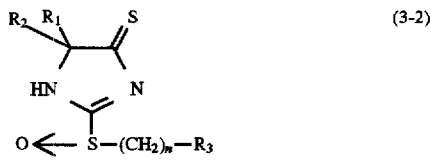

wherein $R_1$, $R_2$, $R_3$ and n are the same as specified in claim 1.

6. An imidazoline derivative or tautomer thereof according to claim 5, wherein $R_1$ and $R_2$ in said formulae (1), (3-1) and (3-2) represent a same one or respective different ones of a hydrogen atom, an alkyl group having 1–7 carbon atoms and a phenyl group, or in combination represent one of an alkylidene group having 2–5 carbon atoms, a benzylidene or cinnamylidene group, and an alkylene group having 2–6 carbon atoms, $R_3$ in said formulae (3-1) and (3-2) representing one of an alkyl group having 1–4 carbon atoms, an alkoxy group having 1–4 carbon atoms, and a phenyl group represented by said formula (2), and wherein $R_4$ and $R_5$ in said formula (2) represent a same one or respective ones of a hydrogen atom, an alkyl group having 1–7 carbon atoms, an alkyl group having 1–7 carbon atoms substituted with at least one halogen atom or at least one hydroxyl group, a cycloalkylalkyl group whose linear alkyl portion has 0–2 carbon atoms and whose cycloalkyl portion has 3–6 carbon atoms, an alkenyl group having 1–7 carbon atoms, an alkanoyl group having 1–7 carbon atoms, an alkanoyl group having 1–7 carbon atoms substituted with at least one halogen atom, an alkoxyalkyl group having 1–7 carbon atoms, an alkoxyalkyl group having 1–7 carbon atoms substituted with at least one halogen atom, an alkoxycarbonyl group having 1–7 carbon atoms substituted with at least one halogen atom, a benzoyl group, a benzyloxycarbonyl group, an alkylaminocarbonyl group having 1–7 carbon atoms, an alkylsulfonyl group having 1–7 carbon atoms, a benzenesulfonyl and a toluenesulfonyl group, while $R_6$ represents one of a hydrogen atom, a hydroxyl group, a halogen atom, an alkyl group having 1–5 carbon atoms, an alkoxy group having 1–5 carbon atoms and a nitro group.

7. An imidazoline derivative or tautomer thereof according to claim 1, wherein $R_3$ is a substituted phenyl group represented by said formula (2) and n is equal to 1.

8. A vulnerary composition comprising a wound-treating effective amount of an imidazoline derivative or tautomer thereof, said imidazoline derivative or said tautomer being represented by the following formula (9),

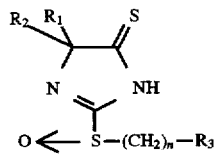
(9)

wherein n represents an integer from 1 to 4, and $R_1$ and $R_2$ represent a same one or respective different ones of a hydrogen atom, a lower alkyl group, a phenyl group, and a benzyl group, or in combination represent one of an alkylene group having 2–6 carbon atoms, an alkylidene group having 2–5 carbon atoms and a benzylidene or cinnamylidene group, while $R_3$ represents a a phenyl group represented by the following formula (10),

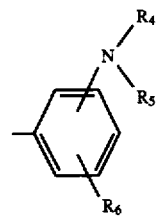
(10)

wherein $R_4$ and $R_5$ represent a same one or respective different ones of a hydrogen atom, a lower alkyl group, a lower alkyl group substituted with at least one halogen atom or at least one hydroxyl group, a cycloalkylalkyl group, a lower alkenyl group, a lower alkanoyl group, a lower alkanoyl group substituted with at least one halogen atom, a lower alkoxyalkyl group, a lower alkoxycarbonyl group, a benzoyl group, a lower alkylaminocarbonyl group, a lower alkylsulfonyl group, a benzenesulfonyl group and a toluenesulfonyl group, while $R_6$ represents one of a hydrogen atom, a hydroxy group, a halogen atom, a lower alkyl group, a lower alkoxy group and a nitro group and a carrier therefor.

9. An ulcer-treating composition comprising an ulcer-treating effective amount of an imidazoline derivative or tautomer thereof, said imidazoline derivative or said tautomer being represented by the following formula (11),

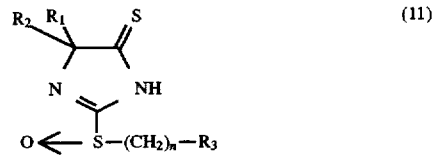
(11)

wherein n represents an integer from 1 to 4, $R_1$ and $R_2$ represent a same one or respective different ones of a hydrogen atom, a lower alkyl group, a phenyl group, and a benzyl group, or in combination represent one of an alkylene group having 2–6 carbon atoms, an alkylidene group having 2–5 carbon atoms, a benzylidene or cinnamylidene group, a benzylidene or cinnamylidene group having an alkylidene group having 2–5 carbon atoms and a benzylidene or cinnamylidene group, while $R_3$ represents a phenyl group represented by the following formula (12),

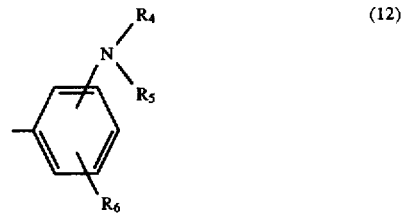
(12)

wherein $R_4$ and $R_5$ represent a same one or respective different ones of a hydrogen atom, a lower alkyl group, a lower alkyl group substituted with at least one halogen atom or at least one hydroxyl group, a cycloalkylalkyl group, a lower alkenyl group, a lower alkanoyl group, a lower alkanoyl group substituted with at least one halogen atom, a lower alkoxyalkyl group, a lower alkoxycarbonyl group, a benzoyl group, a benzyloxycarbonyl group, a lower alkylaminocarbonyl group, a lower alkylsulfonyl group, a benzenesulfonyl and a toluenesulfonyl group, while $R_6$ represents one of a hydrogen atom, a hydroxyl group, a halogen atom, a lower alkyl group, a lower alkoxy group and a nitro group and a carrier therefor.

10. The composition according to claim 9, wherein said imidazoline derivative is 2-(2-N-4-thione).

11. The composition according to claim 9, wherein said imidazoline derivative is 2-(2-dimethylaminobenzylsulfinyl)-5,5-dimethylimidazolin-4-thione.

12. The composition according to claim 9, wherein said imidazoline derivative is 2-(2-N-isobutyl-N-methylaminobenzylsulfinyl)-5,5-dimethylimidazolin-4-thione.

* * * * *